(12) United States Patent
Lee et al.

(10) Patent No.: US 11,213,823 B2
(45) Date of Patent: Jan. 4, 2022

(54) MICROFLUIDIC IN SITU LABELLING ON STABLE INTERFACES

(71) Applicant: The Regents of the University of California, Oakland, CA (US)

(72) Inventors: Abraham P. Lee, Irvine, CA (US); Neha Garg, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 726 days.

(21) Appl. No.: 15/867,522

(22) Filed: Jan. 10, 2018

(65) Prior Publication Data

US 2018/0193836 A1 Jul. 12, 2018

Related U.S. Application Data

(60) Provisional application No. 62/445,171, filed on Jan. 11, 2017.

(51) Int. Cl.
| | |
|---|---|
| *G01N 33/80* | (2006.01) |
| *G01N 15/14* | (2006.01) |
| *G01N 33/574* | (2006.01) |
| *G01N 15/10* | (2006.01) |
| *B01L 3/00* | (2006.01) |

(52) U.S. Cl.
CPC ........ *B01L 3/502761* (2013.01); *G01N 15/14* (2013.01); *G01N 15/1484* (2013.01); *G01N 33/574* (2013.01); *G01N 33/80* (2013.01); *B01L 2200/0652* (2013.01); *B01L 2200/10* (2013.01); *B01L 2300/0861* (2013.01); *B01L 2300/0883* (2013.01); *B01L 2400/0436* (2013.01); *G01N 2015/1006* (2013.01); *G01N 2015/149* (2013.01)

(58) Field of Classification Search
None
See application file for complete search history.

(56) References Cited

U.S. PATENT DOCUMENTS

| | | | |
|---|---|---|---|
| 2013/0171628 A1* | 7/2013 | Di Carlo | C12Q 1/68 435/6.1 |
| 2015/0219623 A1* | 8/2015 | Doria | B01F 13/0059 435/29 |

OTHER PUBLICATIONS

Patel, Marulik V. et al., Cavity-induced microstreaming for simultaneous on-chip pumping and size-based separation of cells and particles, 2014, Royal Society of Chemistry, 14, 3860-3872 (Year: 2014).*

* cited by examiner

*Primary Examiner* — Jill A Warden
*Assistant Examiner* — Brittany I Fisher
(74) *Attorney, Agent, or Firm* — Knobbe, Martens, Olson & Bear, LLP

(57) ABSTRACT

A method of trapping constituents of interest in a fluid sample flowing through a microfluidic channel by vibrating an interface of the fluid sample and a gas occupying a lateral channel adjacent the microfluidic channel is described. A marker is flowed into the microfluidic channel such that the marker bonds with constituents of interest. The constituents of interest bonded to the marker can help identification of the constituents of interest.

14 Claims, 29 Drawing Sheets

MICROFLUIDIC IN SITU LABELLING ON STABLE INTERFACES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application is directed to devices and methods for performing in situ labelling of trapped cells and for stabilizing air-liquid interfaces in microfluidic devices including lateral cavity acoustic transducers (LCATS) to enable longer operating times for LCATs.

Description of the Related Art

Biological sample preparation can involve the process of reducing the complexity of a patient's sample by removing non-target components and by extracting a target analyte. Whole blood is one of the most complex and diverse fluids harboring massive amount of information about the functioning of human body, thus making the analysis theoreof a prime interest for both diagnostic and scientific applications. One can think of blood as being composed of two main components: plasma and cells. Different cells in blood perform different and specific functions in different conditions. Thus, different analyses may make one or only some of the cells as of interest. It is desirable in certain analyses to isolate and separate these cells of interest from rest of the whole blood.

Red blood cells (RBCs), white blood cells (WBCs) and platelets are prominent cells in whole blood. There are around a billion RBCs along with platelets and a million WBCs per mL of whole blood and each of them vary in size. Platelets are about 1-3 µm in diameter while RBCs are 6-9 µm. WBCs are the largest of all and vary from 9-20 µm. Because these cells are generally non-overlapping in their size ranges, size based separation techniques can be employed to isolate them.

Flow Cytometry is a laser based biophysical technique used in pathology to sort and identify cells. However, due to the high cost and requirement of skilled technician, microfluidics and miniaturized lab-on-chip type devices hold potential for simpler and more cost effective blood analyses.

SUMMARY OF THE INVENTION

Apparatuses and methods described herein can stabilize microbubbles in a microfluidic device. Microbubbles can be understood to include an air-liquid interface. The air-liquid interface can be stabilized by increasing the capillary number of the liquid. A sample (e.g., particles or cells) in the liquid can be trapped in vortices generated when the air-liquid interface is actuated by piezoelectric transducer (PZT) or otherwise oscillated. In situ labelling of the sample (e.g., particles or cells) trapped in the vortices can be performed.

Owing to these differences in diameter, size based separation in lateral cavity acoustic transducers (LCAT) can be used to separate whole blood into its constituents. A LCAT device can include one or a series of microbubbles as discussed further below.

An innovative aspect of the subject matter of this application is embodied in a method for visualizing cells in a blood sample. In the method a volume of the blood sample is introduced into a microfluidic device. The microfluidic device comprises a channel that extends from an inlet past an array of cavities disposed along the length of the channel. The channel can be a microfluidic channel. Each of the cavities is enclosed on one end and exposed to the microfluidic channel at a junction opposite the enclosed end such that each of the cavities can be occupied by gas that forms an interface with a liquid flowing through the microfluidic channel. The gas can comprise a microbubble. The method further comprises oscillating a gas-liquid interface at the junction of each of the cavities to trap blood constituents of interest in the microfluidic channel adjacent to the junction in a microstreaming flow pattern. The method further comprises introducing a marker into the microfluidic channel upstream of cavities. The blood constituents of interest are exposed to the marker for time sufficient to cause the blood constituents of interest to couple or to bond with the marker. The method further comprises imaging the markers bonded with the blood constituents of interest to identify the presence or concentration of the blood constituents of interest in the blood sample.

Another innovative aspect of the subject matter of this application is embodied in a method of identifying constituents of a sample. The method comprises flowing a first liquid into a lateral channel acoustic transducer (LCAT) microfluidic device. Constituents of interest are trapped in a main channel of the LCAT microfluidic device adjacent to lateral channels thereof by oscillating the LCAT microfluidic device. A marker flows into the LCAT microfluidic device while the constituents are trapped, such that the marker combines, e.g., bonds, with constituents of interest. A number of, e.g., a concentration of, the constituents of interest is identified by the number of, e.g., a concentration of, markers present in an output of the sample, e.g., a portion of the sample, following the flowing of the marker into the LCAT.

Yet another innovative aspect of the subject matter of this application is embodied in a point-of-care device comprising an LCAT device. The LCAT device comprises a main channel and at least one lateral channel configured to enclose a volume of gas; and a vibration inducing device include a function generator to cause vibrations to be applied to the LCAT. The point-of-care device also includes a marker component configured to flow through the main channel to interact with one or more sample constituents trapped by the LCAT device to cause the sample constituent to be visualizable.

Another innovative aspect of the subject matter of this application is embodied in a method for visualizing matter within a microfluidic device. In the method a first liquid flows into a microfluidic channel to a location of the microfluidic channel exposed to a cavity of the microfluidic device. The cavity is occupied by a gas. The microfluidic device is vibrated to oscillate a gas-liquid interface at the location of the microfluidic channel exposed to the cavity. A circulating flow is created by the vibration at the location of the microfluidic channel exposed to the cavity. Constituents of interest of the first liquid are trapped in the circulating flow at the location of the microfluidic channel exposed to the cavity. A marker flows into the microfluidic channel to the location of the microfluidic channel exposed to the cavity. The marker combines with, e.g., bonds with, constituents of interest. Constituents of interest bonded to the marker are identified by visualizing the marker.

In another embodiment, a method of improving size based separation of like sized constituents of a liquid mixture is provided. A size incrementing component is combined with a first constituent of a liquid mixture. The size incrementing component is not combinable with a second constituent of the liquid mixture. The first and second constituents are like sized prior to the combination of the first constituent with the size incrementing component. The liquid mixture flows into a microfluidic channel. The mixture travels to a location within the microfluidic channel that is exposed to a cavity of the microfluidic device. The cavity is occupied by a gas. The microfluidic device is vibrated to oscillate a gas-liquid interface at the location where the microfluidic channel is exposed to the cavity. This vibration creates a circulating flow at the location where the microfluidic channel is exposed to the cavity. The circulating flow allows capturing the first constituent that is combined with the size incrementing component, but not the second constituent. The second constituent is released from the system.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of the drawings.

DETAILED DESCRIPTION OF THE PREFERRED EMBODIMENT

This application is directed to improving LCAT devices and methods and point-of-care apparatuses that can employ such devices. Such improved methods and apparatuses can include both sorting cells, particles and other solid sample constituents and staining or otherwise enhancing the identification of target cells, particles or solid sample constituents of interest for further analysis (e.g., by fluorescent labelling). Such improved methods can also involve adapting the LCAT device to be capable of operating for extended periods of time in connection with procedures to find rare cells in a sample, e.g., cells at concentrations of 10 cells/milliliter. Such improved methods can also involve combining cells of interest with a substance where the combined size enables the cell of interest to be separated from other cells of similar size that are not of interest.

Figure 1:
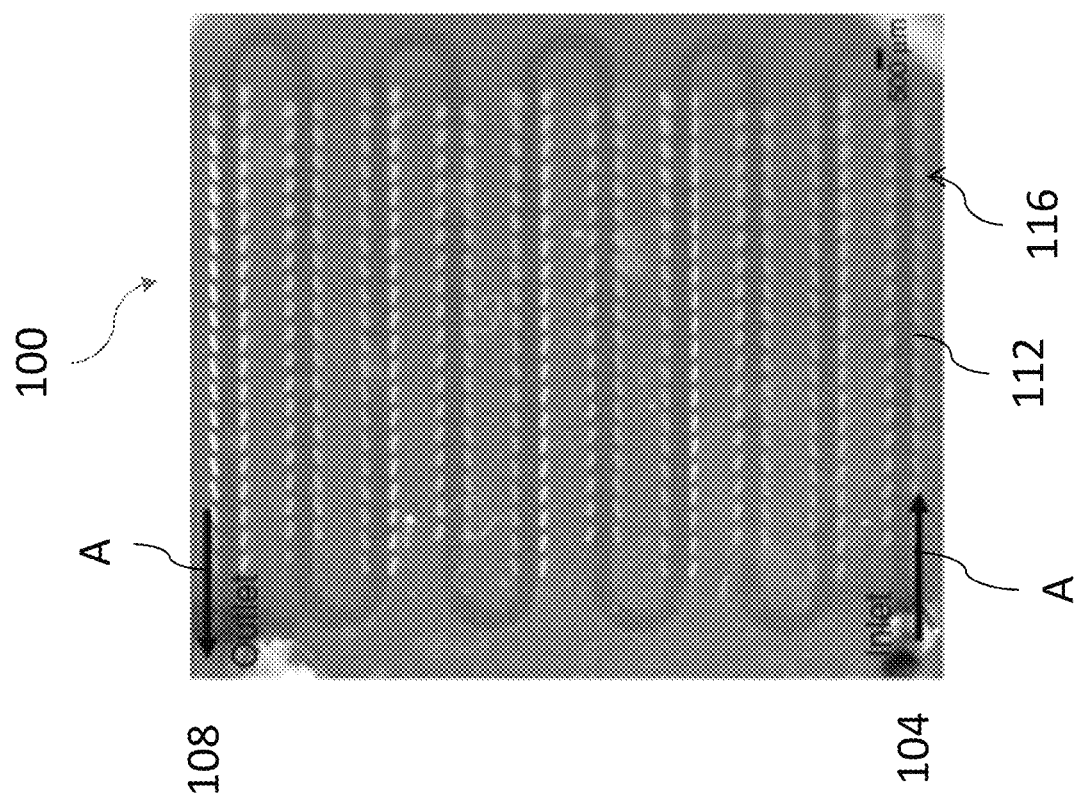
FIG. 1 is an enlarged image of an LCAT device.
Figure 2:
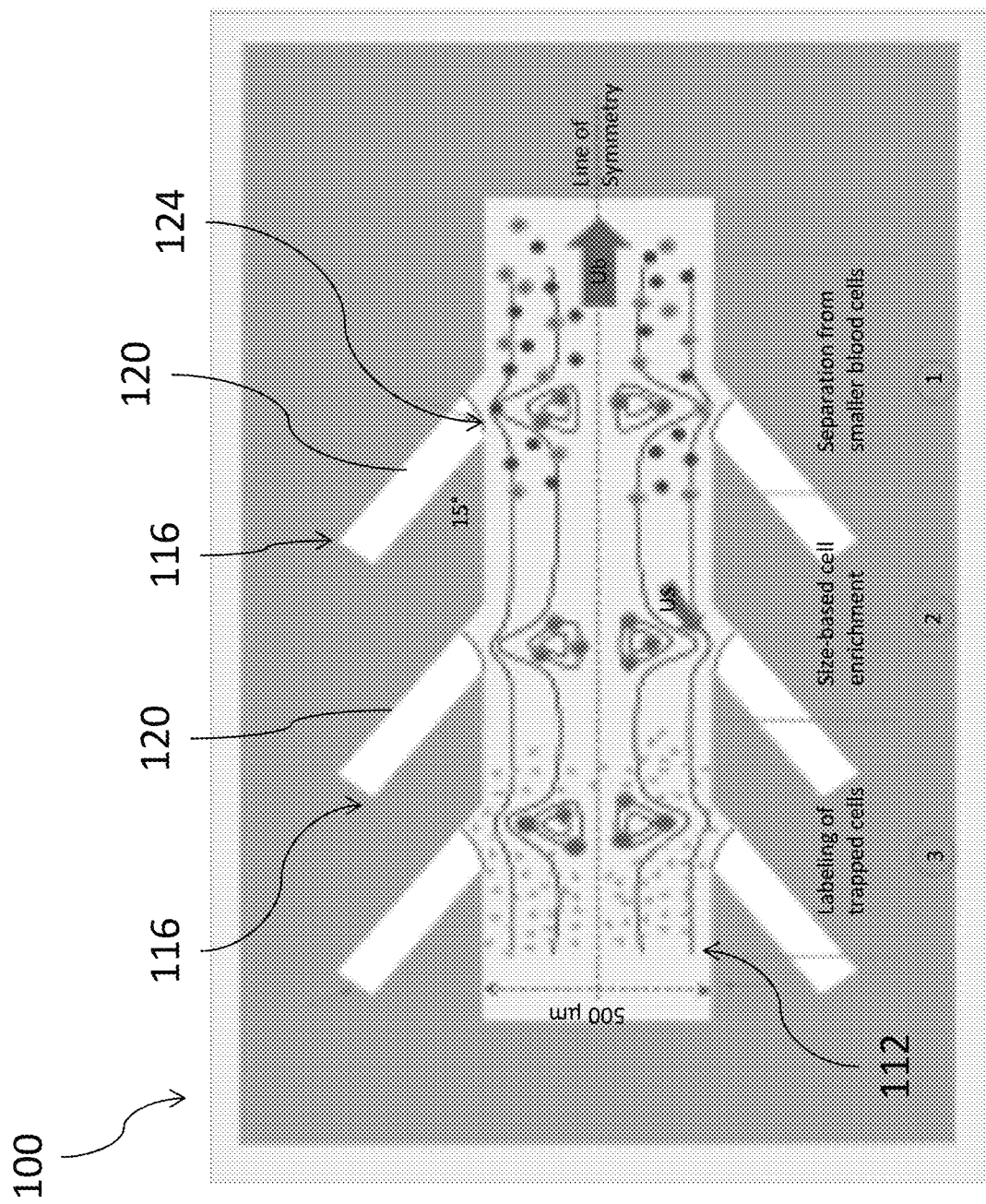
FIG. 2 is a schematic illustration of a segment of the LCAT device of FIG. 1, illustrating fluid flow properties and particle trapping behavior in one operating regime of the LCAT device.

FIGS. 1 and 2 show an example LCAT microfluidic device 100. The device includes an inlet 104, an outlet 108, and at least one main channel 112. The main channel 112 can take any suitable form but in certain embodiments has a serpentine form. The serpentine channel 112 provides a long flow path within a small area for exposing the fluid sample to a large number of LCAT interface sites 116 along the direction of arrows A.

The LCAT device 100 exploits acoustic microstreaming to separate and enrich constituents of interest, e.g., cells and/or particles. Acoustic microstreaming is a phenomenon in which localized streaming patterns occur near an oscillating surface. Here, the acoustic microstreaming is based on the actuation of the gaseous bubbles using an acoustic energy source. The LCAT device 100 can comprise of one or an array of dead-end side channels 120 (see FIG. 2) located at discrete spaced apart LCAT interface sites 116. Air can be trapped in these dead-end side channels 120. The trapped air behaves like a bubble, which is defined at one end by an air-liquid interface 124. The actuation of these bubbles (or bubble) in liquid phase by the acoustic energy source leads to a first-order periodic flow within the fluid and the magnitude of the excited flow at the boundary is given by:

$$U_0 \sim d\omega$$

Where, $U_0$ is the first characteristic flow velocity of cavity induced microstreaming which is velocity of oscillating flow due to oscillatory motion of the air-liquid interface 124 in response to incident acoustic wave, d is the interface displacement amplitude and $\omega$ is the angular frequency of the acoustic field. The first order periodic flow induces a steady second-order streaming flow within the boundary layer near the air-liquid interface 124 whose magnitude is given by $$U_s \sim U_0^2/\omega R$$

Where, $U_s$ is the second-order characteristic velocity of streaming flow which arises due to the net displacement of fluid parcels during each oscillation cycle of the air-liquid interface 124, and R is the equivalent radius of the air-liquid interface 124.

More particularly to FIG. 2, a segment of the main channel 112 is shown. In this segment, lateral channels 120 are disposed on both sides of an axis of symmetry of the main channel. The air-liquid interface 124 is formed in each of a plurality of lateral channels 120 at each of the LCAT interface sites 116. The width of the main channel 112 is shown to be 500 micron but can be other sizes. Upstream of the lateral channels 120 (to the left on the figure), there is a mix of particles of different sizes, some of interest and some not of interest. As the fluid containing these particles flows into the vicinity of the channels 120 the particles encounter micro-streaming which causes larger particles to be trapped in circulating flow. The circulating flow can be generated by vibrating the air-liquid interface 124, such as, for example by using a piezo-controlled actuator. By virtue of the fluid flow properties, smaller particles are allowed to flow past the circulating flow. This allows the smaller particles, e.g., platelet and red blood cells to continue to flow with the bulk flow $U_b$ downstream and out of the vicinity of the channels 120.

FIG. 2 shows that the channels 120 can be disposed at an angle, e.g., at about 15 degrees, to the main channel 112. This can beneficially cause the bulk flow $U_b$ to arise without the need for an external pressure source. In other applications, an external pressure source (e.g., a syringe pump) can be used with the channels 120 being at the same or at other angles.

Figure 3:
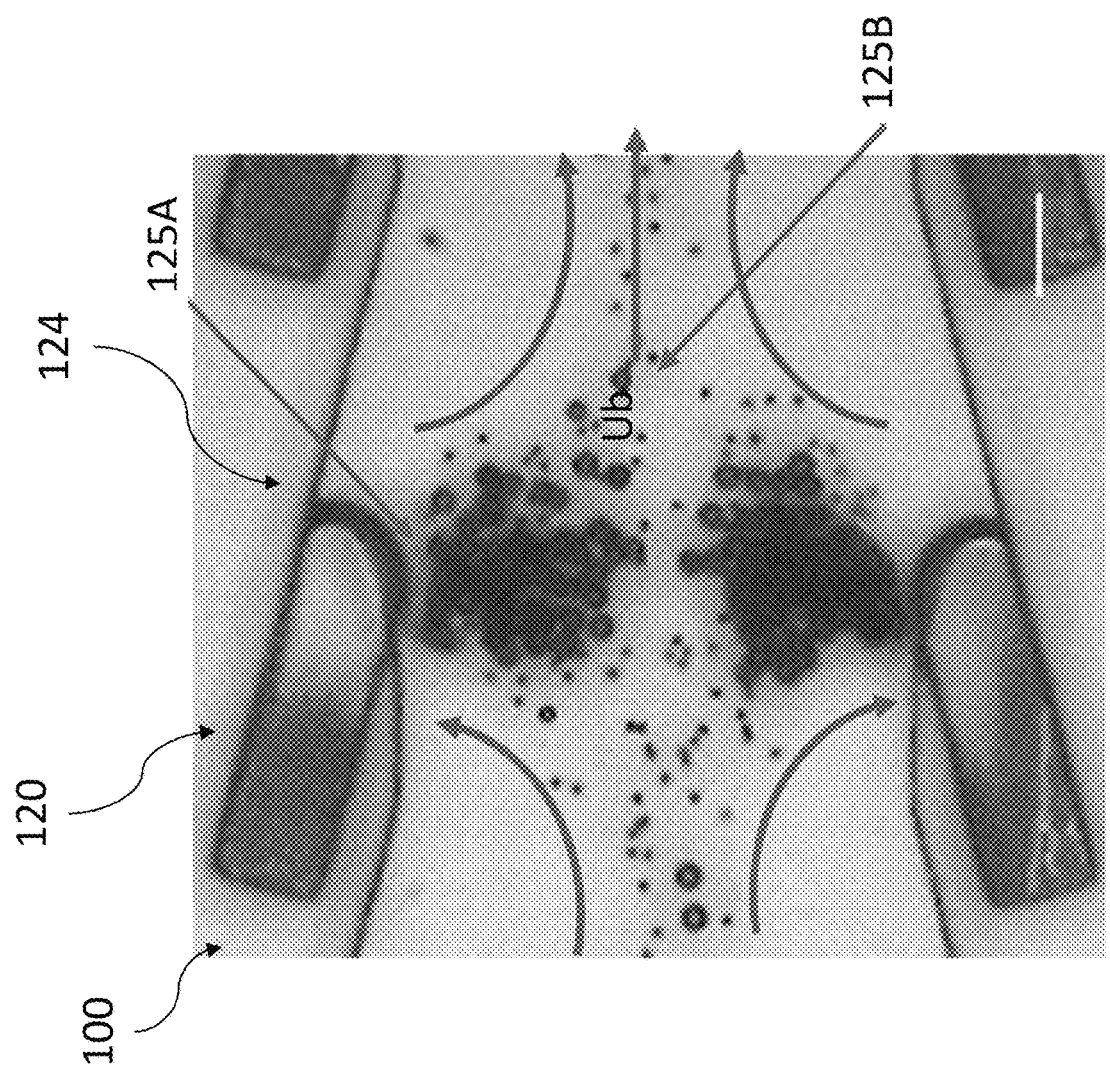
FIG. 3 is a microscopic image of the flow behavior illustrated in FIG. 2 in an actual LCAT device, wherein larger particles are trapped in a circulating flow pattern and smaller particles are permitted to flow along with bulk flow.

FIG. 3 shows how larger particles will separate from smaller particles in a segment of the main channel 112 that is shown. In this segment, 25 µm particles 125A become trapped in closed circular streamlines, while 10 µm particles 125B pass through the channel.

Enrichment Ratio

An enrichment ratio (ER) is used as a metric to analyze the device performance. It is defined as the enhancement of target cell to background cell ratio from the device input to the output sample.

$$\text{Enrichment Ratio } (ER): \frac{(\text{target cells/background cells})_{output}}{(\text{target cells/background cells})_{input}}$$

An ER approximately 100× to 1000× is clinically significant for subsequent gene profiling by RT-PCR. In experiments, the device has an ER of 170× for a particle mixture consisting of 15 and 10 µm at initial ratio of 1:100,000. The device has achieved a 213× enrichment of MCF-7 cells with respect to WBCs when spiked at 10 ml$^{-1}$ in whole blood while ensuring the capturing of all target cells and thus avoiding false negatives.

EXAMPLE METHODS

Figure 4A:
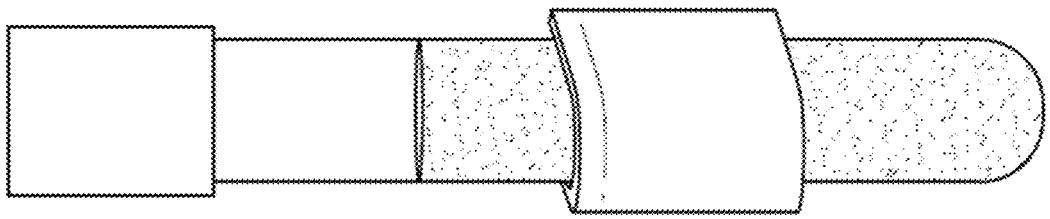
FIGS. 4A-4C illustrate particle sorting capabilities of the LCAT devices disclosed herein.
Figure 4A:
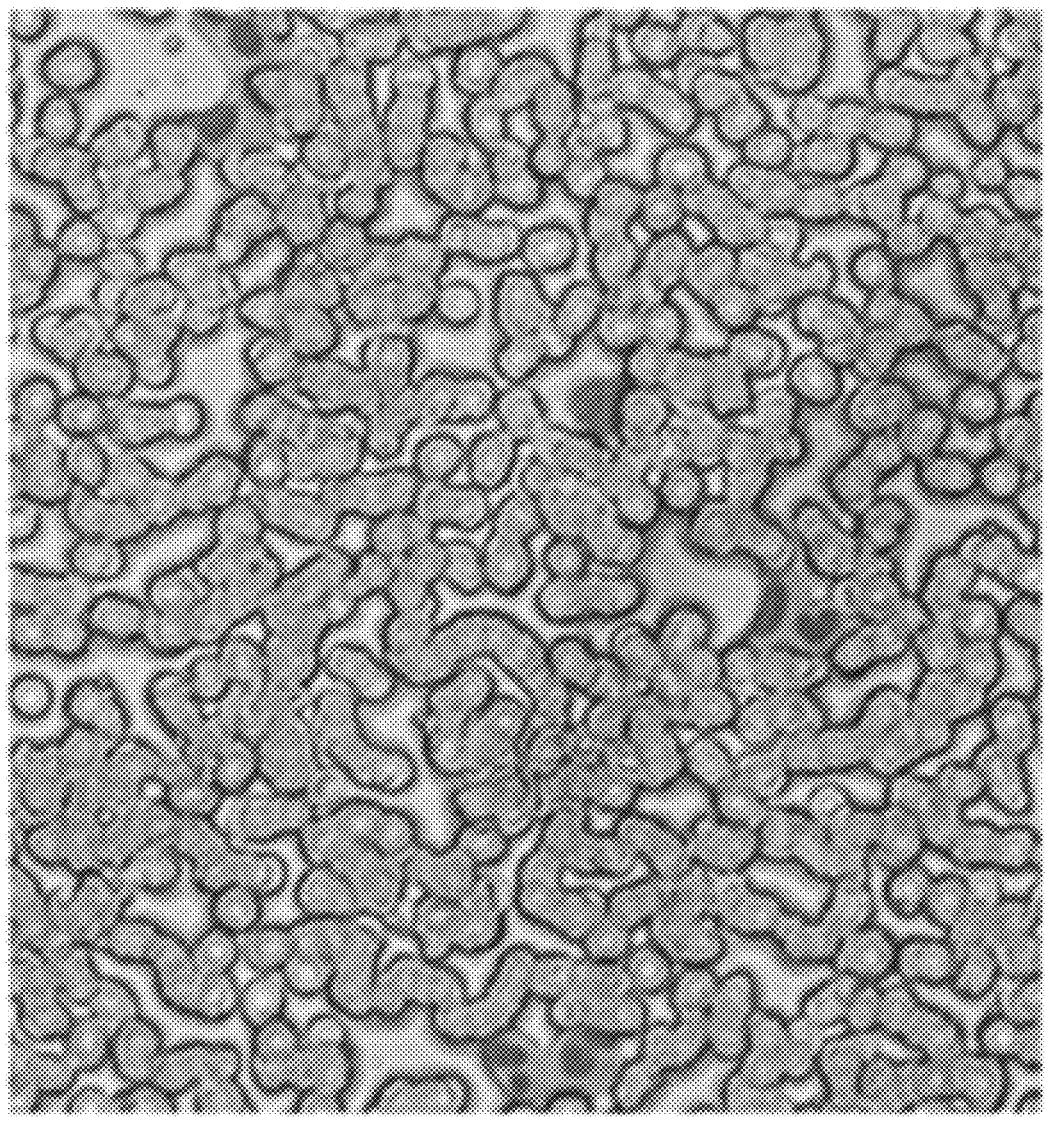
Figure 4B:
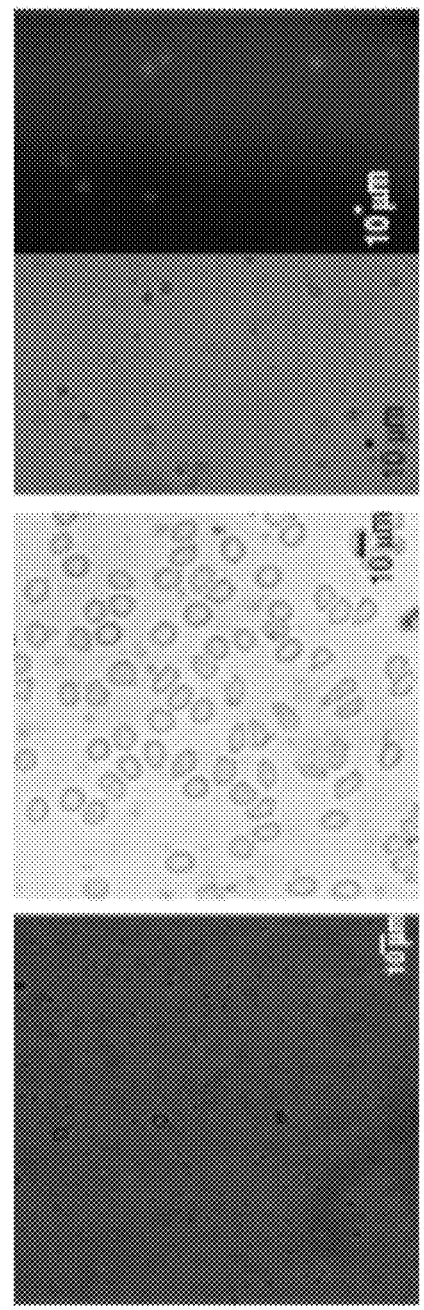

In one embodiment, the LCAT device 100 of FIG. 1 was first primed with 1× Phosphate-buffered saline (PBS buffer) with a syringe to form air-liquid interfaces 124. The LCAT device 100 was placed on a piezoelectric transducer (PZT) with an ultrasound gel smear disposed there between. The inlet 104 of the device was punched with a 4 mm punch and the outlet 108 was cut to collect each cellular constituent with a pipette. 30 µL of the whole blood was poured in the inlet 104 and the interfaces 124 were actuated at 2 Vpp from a function generator. Due to the bulk flow ($U_b$) generated by the device 100, the pumping started from inlet 104 to the outlet 108 and larger cellular components (compared to platelets), e.g., RBCs and WBCs, were trapped in microstreaming vortices because of streaming flow ($U_s$). This arrangement resulted in 1-2 µL plasma mixed with platelets being extracted and collected from the outlet 108. RBCs were released from the traps (formed by the vortices at the LCAT interface sites 116 after increasing the voltage to 2.5 Vpp to increase the $d_{gap}$ and collected from the outlet 108. Without any loss of generality the parameter $d_{gap}$ as used herein refers to the minimum distance between an outer flowline of the microstreaming vortices and the air-liquid interface 124. In the process, extra blood sample was removed and the inlet 104 was filled with 30 µL PBS as wash buffer. After washing the device three times and collecting RBCs from the outlet 108, voltage was further increased to 4.5 Vpp to release WBCs that were trapped in the vortices at the LCAT interface sites 116. Plasma with platelets was viewed in bright field at 40× on a countess slide while whole blood, while RBC and WBC samples were stained using standard protocol for Wright-Giemsa smear stain (FIGS. 4A and 4B). FIG. 4A shows a standard vial of whole unprocessed blood (right) and a Wright-Giemsa smear stain of the blood (left). The Wright-Giemsa stains typically stain the cytoplasm of cells an orange to pink color, while dark blue areas generally correspond to nuclear areas. FIG. 4B shows the bright field image of a vial of plasma containing platelets (left). In comparison, the middle image shows an RBC sample after sorting from the device. The far right image shows bright field and fluorescent imagining of the WBC sample after sorting by the device and staining with DAPI.

In one embodiment cell counting was done using image processing software (e.g., imageJ) in each image which shows that plasma sample consists approximately 95% platelets, RBC sample consists of 98% RBCs and WBC sample consists of approx. 78% WBCs.

Figure 4C:
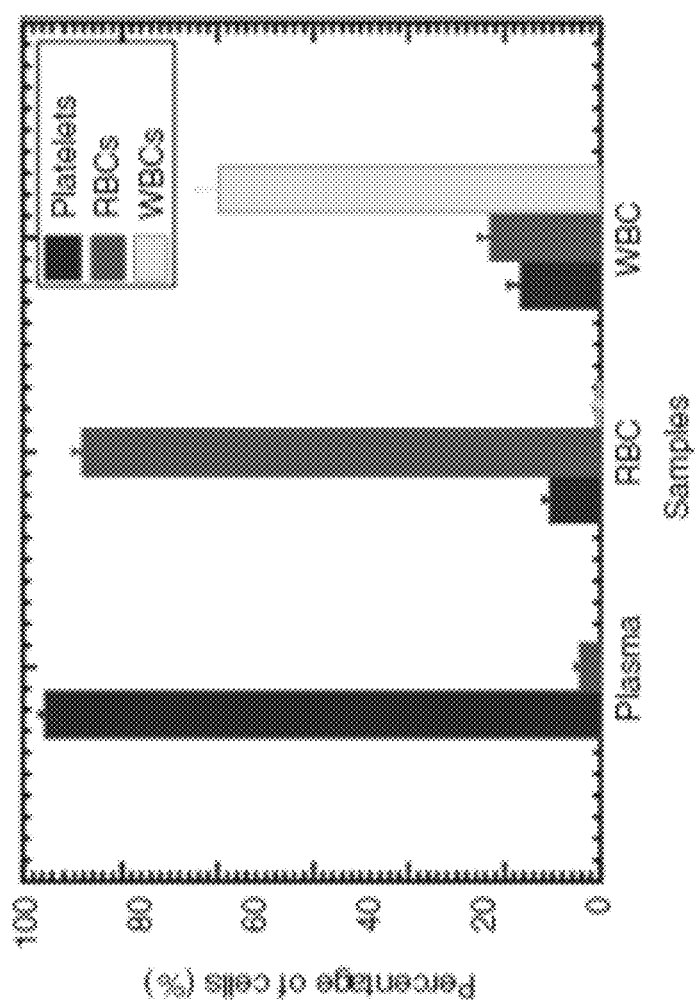

In another embodiment cell counting was done using image processing software (e.g., imageJ) in each image which shows that plasma sample consists approximately 96.3% platelets, RBC sample consists of 90.8% RBCs and WBC sample consists of approx. 66.4% WBCs (FIG. 4C).

In-Line Cell Labeling

In some cases, rare cells such as circulating tumor cells or cancer-associated fibroblasts also exist in our circulatory system. Separation and enrichment of these rare cells from unprocessed blood specimen is of prime interest for both prognosis and treatment monitoring. To mimic the rare cells in blood, MCF-7 breast cancer cell line can be spiked in whole blood. Post-separation analysis of target cells can include identification, enumeration and characterization. Both identification and enumeration can be performed by immunofluorescence. Immunofluorescence is resistant to presence of non-target cells in the output sample. Till today, despite considerable automation, along with blood handling and separation, detection by immuno-staining of target cells is performed manually.

While the standard staining procedure takes time (at least 1 hour), it also requires expensive centrifuge devices for washing. The benefits of clinical lab assays may be enhanced if the lab results can be obtained rapidly in a point-of-care manner. Therefore, to maximize the utility of lab-on-chip devices in point-of-care setting, we propose to combine size based separation with biomarker expression. This will lead to the complete hematological separation along with detection of target cancerous cell by immunolabeling. This will lead to reduction of turnaround time and equipment expenses.

Figure 5A:
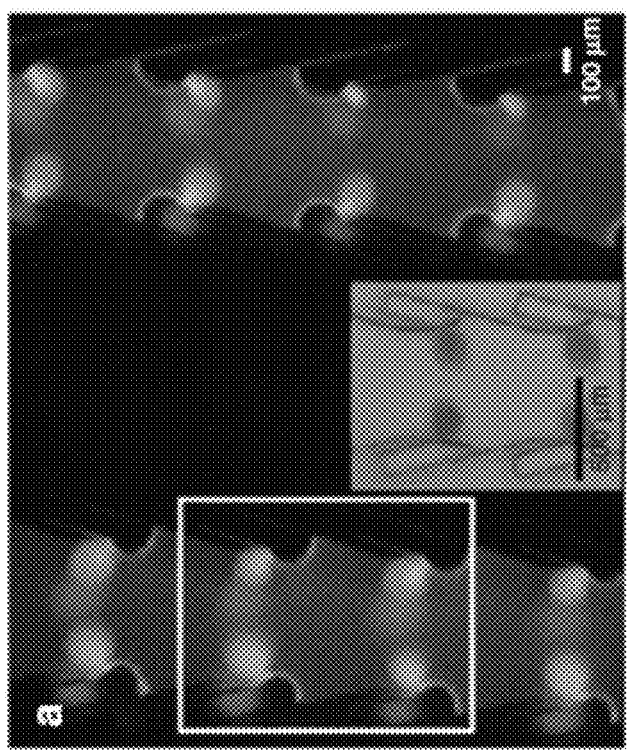
FIGS. 5A-5D show effective in-situ labeling of cancer cells in whole blood by use of an LCAT device.
Figure 5B:
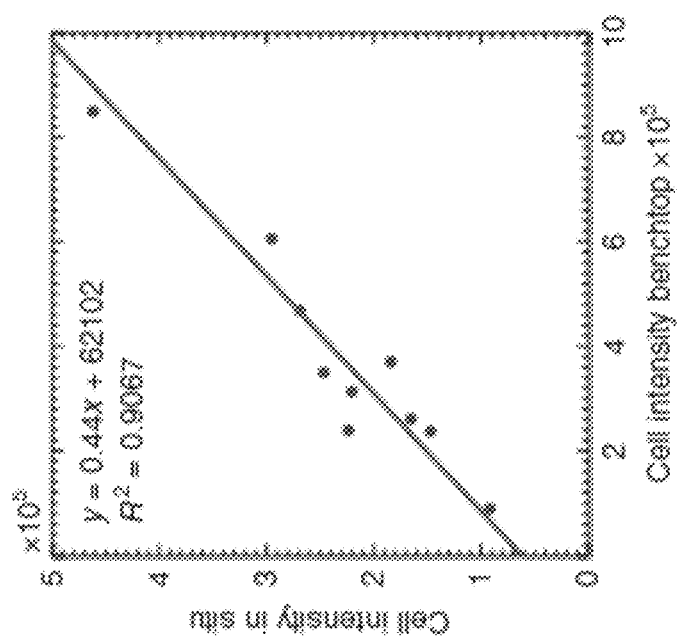

Keeping this in mind, in an example method we trapped in vortices at the LCAT interface sites 116 a pure MCF-7 cell population in suspension. We then stained the MCF-7 cells with anti-epithelial cell adhesion molecule (EpCAM) antibody conjugated to a tandem fluorophore, sold under the trade name PE-Dazzle™. 30 µL of MCF-7 cell suspension was pumped at 2.5 Vpp from the inlet 104 of the LCAT device 100 for 5 min. After the cells were trapped in microstreaming vortices at the LCAT interface sites 116, 20 µL of Fc block was added in the inlet 104 after removing the extra cell sample. Fc block was flowed for 5 min followed by pumping 4 µL of CD326 (anti-EpCAM) antibody for 5 min. To prevent the main channel 112 from sucking air (i.e., from drawing the air out of the side channels 120 and depleting the air bubbles therein), 30 µL of staining buffer was added after 2 min in the inlet 104 to wash the unbound antibodies. The cells were thus immunolabeled on the device 100 within 20 min. The fluorescent labeled MCF-7 cells were then imaged using a fluorescent upright microscope as shown in FIG. 5A. FIG. 5A shows in the boxed close up, the fluorescent imagining of stained MCF-7 cells concentrated within highly pure vortices within the channel of the device. We correlated the MCF-7 cells stained using standard benchtop procedure of 50 min with immunostaining in situ for 20 min. Approximately 91% correlation shows the comparable fluorescent intensity of the cells demonstrating that the expression level of the cells is similar (FIG. 5B).

Figure 5C:
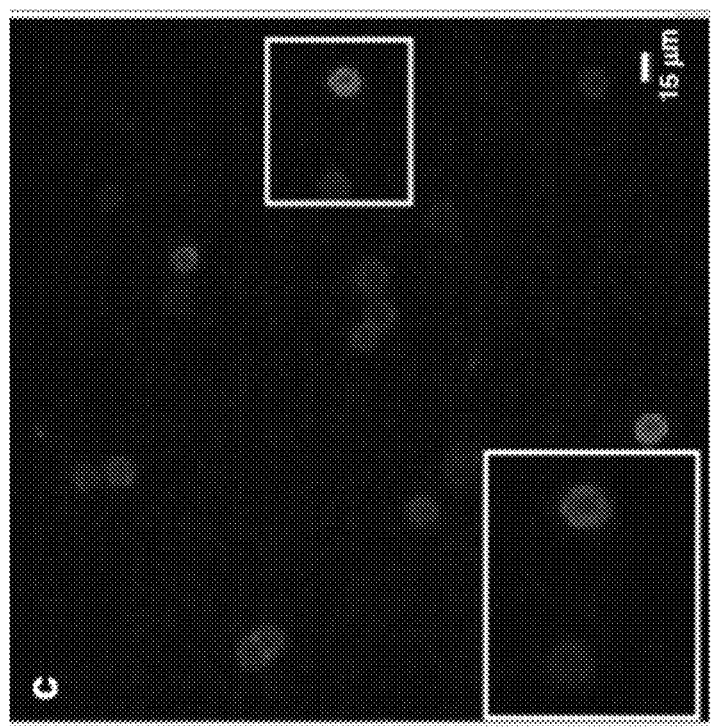
Figure 5D:
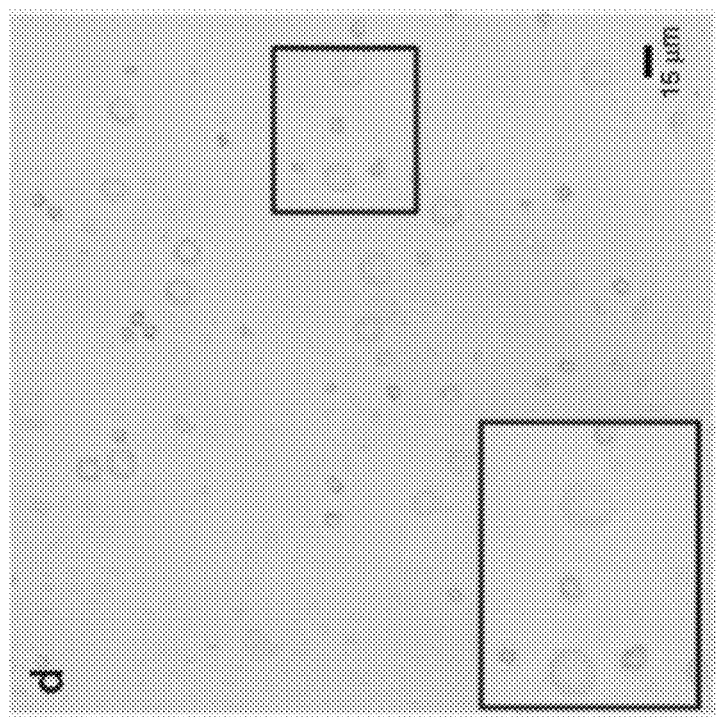

After improving the immunostaining protocol, in another example we pumped MCF-7 cell spiked whole blood in the device 100. The sample had 50,000 cells of MCF-7 per mL of whole blood. Platelets and RBCs were first extracted, followed by pumping 30 μL of RBC lysing buffer for 5 min to ensure complete removal of RBCs from the microstreaming vortices. As a result, a mixture of remaining WBCs and MCF-7 cells were circulating at the air-liquid interfaces 124. At this point, we stained the MCF-7 cells selectively on device using the similar protocol demonstrated above and released the mixture at 4.5-5 Vpp. The released sample was imaged in a countess slide on a fluorescent microscope. The fluorescently labeled cells were imaged at TRITC filter (FIG. 5C). FIG. 5C shows fluorescent image of MCF-7 cells after sorting, enriching, and on-chip labeling. FIG. 5D shows a bright field image of the released sample. Within the boxes are close up images of the smaller WBCs and larger MCF-7 cells. This example demonstrated an approximate ER ratio of 10× for fluorescently labeled MCF-7 cells with respect to WBCs and confirms the identification and enumeration of target cancer cells specifically based on both size and marker expression, which is particularly important for clinical blood samples.

These examples show the effectiveness of sorting and imaging large cells, such as cancer cells and other rare cells that might be in a sample.

Further Methods

Surface tension is an important parameter in the behavior of fluids in LCATs and other devices operating at microscale, influencing the stability and size of microbubbles. Accordingly, measuring surface tension is useful. Surface tension measurement involves imaging the shape of an inert fluid drop or meniscus. However, current instrumentation for making these measurements are not intended for and not well suited to make measurements at microscale. Such current instruments may not account for the effects of fluid flow on surface tension inside microfluidic devices.

A number of microfluidic measurement approaches have been published in literature, deriving surface tension from droplet deformability, production size, or production rate. Measurement of droplets deformability and size, however, can be influenced by microscope focus. Measurement of production rate using fiber-optic detection seems limited to bubbles.

The methods and structures disclosed herein enhance the performance of an LCAT microfluidic device by increasing the durability of the air-liquid interface formed therein. Having more durable air-liquid improves the usefulness of the LCAT microfluidic device at least in allowing for more stable sample capture and retention. The air-liquid interface can be used to trap particles, including biological cells for analysis as discussed above. For example, the air-liquid interface can be vibrated using a piezo controller to generate vortices in the liquid. The size of the vortices generated can be controlled by controlling the amplitude and/or the frequency of vibration of the air-liquid interface. Without relying on any specific theory, the size of the particles trapped in the vortices can depend on the size of the vortices generated and/or the minimum distance between an outer flowline of the generated vortices and the air-liquid interface. Thus, the size of the particles that are trapped in the vortices can be controlled by controlling the size of the vortices which in turn can be controlled by controlling the amplitude and/or the frequency of vibration of the air-liquid interface. In various embodiments, the size of the particles to be trapped in the vortices can be increased by linking the particles to be trapped with antibodies that results in an increase in the size of the particles.

In one method, DI water can disposed in the LCAT microfluidic device 100. Outward expansion of air trapped in the side channel can be caused by actuating the interface 124. In one method, such expansion was observed within 5 minutes of PZT actuation. Without being bound to any specific theory, the inventors of the inventions disclosed herein believed that the air expanded when the water at the interfaces caused micro-droplets to be formed inside the trapped air. The micro-droplets increased the pressure in the side channel 112 which caused the gas-liquid interface 124 to bulge.

It is desirable to increase the stability of the gas-liquid interface 124. One way to increase the stability at the interface 124 is to decrease the surface tension at the interface 124. Surface tension at the interface 124 can be decreased by increasing the capillary number at the interface. For example, lipids can be used to decrease the surface tension at the interface 124 by increasing the capillary number at the interface 124. Other methods of increasing the capillary number could be used as well. To further increase the capillary number, a high viscosity fluid can be added. For example, Glycerol can be used in some methods.

In one example, a mixture of lipid+10% (v/v) glycerol was used to prime and form the interface 28. In one example, the lipid used was DSPC (phospholipid)+DSPE-PEG (lipopolymer emulsifier) (9:1 molo/o). In one example we added 5 mg DSPC+1.96 mg DSPE-PEG2000(9:1 mol %) into 20 ml glass vial. We further added 2-3 ml of Choloroform to dissolve the lipids and make a homogenous solution. In one example, Chloroform was then evaporated using Nitrogen gas until a lipid bilayer was formed on the walls of vial. In one example, 4 ml filtered ultra pure DI water was added into glass vial and sonicate for 20 minutes. The sonication can be at elevated temperature, for example at 45-55° C. In one example, green colored dye mixed in the DI water was added to track the movement in the tubing while applying negative pressure downstream of the channel 12, e.g., by pulling it in syringe.

After the interface 124 is stabilized particles, e.g., cells, of interest can be trapped in stable bubbles, e.g., by way of microvortices. Larger cancer cells (>15 μm) can be trapped in the vortices while smaller cells can pass by due to the bulk flow rate and not be trapped.

In one technique following increasing the stability of the air-liquid interface, in situ fluorescent labelling of trapped cells can be provided. For example, a fluorescent tagged antibody for a specific marker of the cell (e.g., EpCAM) can be introduced in the device 100 with the help of a syringe pump or other positive pressure device. These antibodies will link to the markers expressed on the membranes of the trapped cells and the fluorescence can be observed. These antibodies also will link with smaller cells that express these markers and help in the trapping of these smaller cells. The antibody linking can lead to size increment of smaller cells. The smaller cells can be cancer cells in some cases.

Figures 6A, 6B:
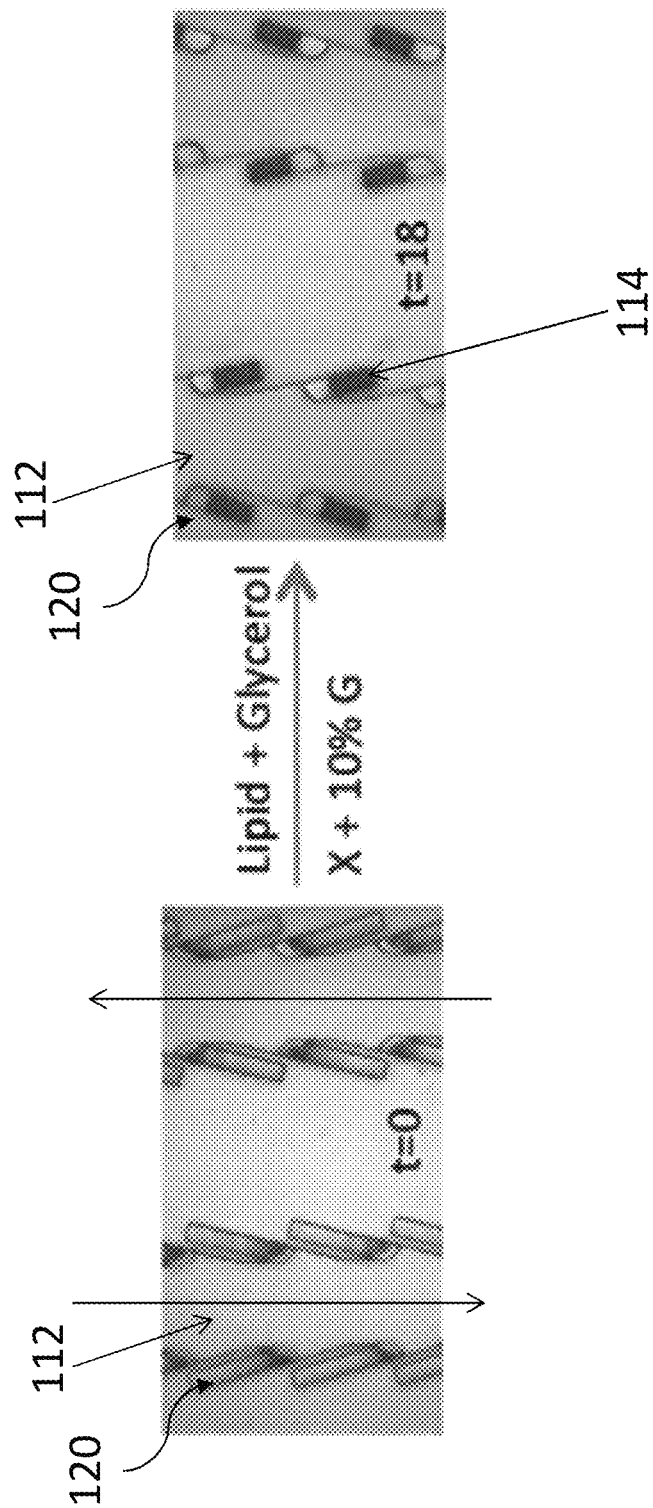
FIGS. 6A and 6B show the stability of the liquid-air interface formed in an LCAT device.

Stable interfaces enclosing air bubbles can enable the viewing of markers expressed by the larger cancer cells. The interfaces formed by the gap enclosed in the lateral channels 120 and the liquid in the main microfluidic channel 112 can be stable for a considerable time duration. FIGS. 6A and 6B show the interface formed by a liquid comprising a mixture of lipid and glycerol and air. FIG. 6A illustrates the image of the interface when they were formed (e.g., at time t=0). FIG. 6B illustrates the image of the interface after about 18 minutes had elapsed. As seen from FIGS. 6A and 6B the liquid-air interface is stable even after 18 minutes. The darker regions observed in FIG. 6B can be attributed to condensation (114) on/in the LCAT device. As time increases, condensation can increase as the material of the LCAT device (e.g., PDMS) can be permeable to air and/or due to PZT vibration.

Device Enhancement for Rare Particle Concentration

Figure 7A:
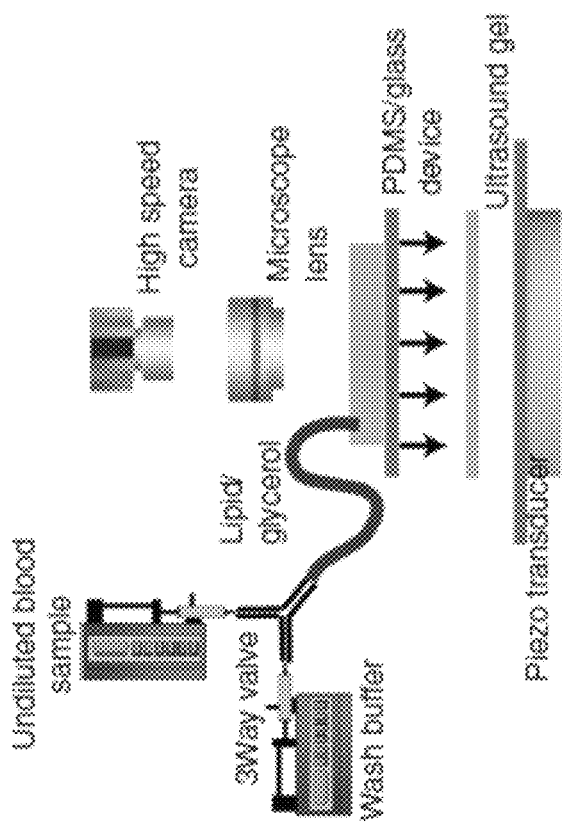
FIGS. 7A-7E show the effective use of a pump to aid in isolating rare particles from a large sample.

Since rare cell detection requires a large sample volume to process, enumerate and analyze, an external syringe pump may be used. The set-up in FIG. 7A shows two syringe pumps connected with a three-way valve for controlling the flow of undiluted blood sample and the wash buffer. It is desirable to increase, improve, or optimize the ER by adjusting the flow rate and voltage before sorting cells.

Figure 7B:
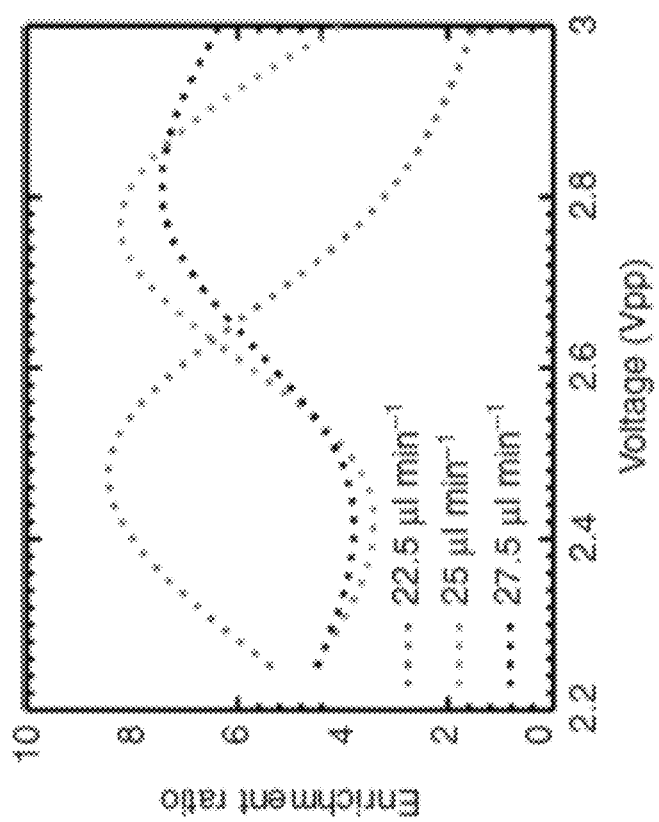

In one example, the ER was evaluated by utilizing polystyrene microparticles of varying sizes that resembled cell diameters and concentrations of rare cells and WBCs in whole blood. First, the LCAT device was primed with an aqueous solution of 10% glycerol in lipid to maintain the stability of air-liquid interfaces and increase the time of operation. Fifteen µm particles were spiked at a concentration of 10,000 particles/ml in a solution containing 1,000,000 particles/ml of 10 µm particles. FIG. 7B shows that the highest ER of 8.5 occurred with a flow rate of 25 µL/min and voltage of 2.75 Vpp. At constant flow rate, $U_b$ by the syringe pump, the ER reduces at larger voltage values (reduced $U_b/U_s$) due to non-specific trapping of 10 µm particles. However, at low voltage values (larger $U_b/U_s$), due to partial release of target 15 µm particles, a reduced ER is observed.

Figure 7C:
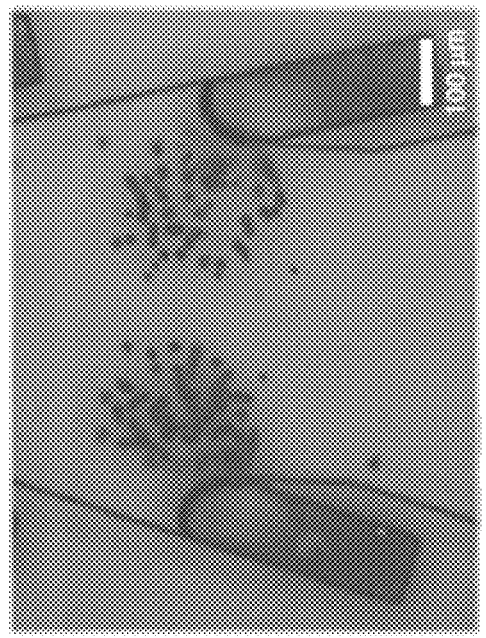
Figure 7C:
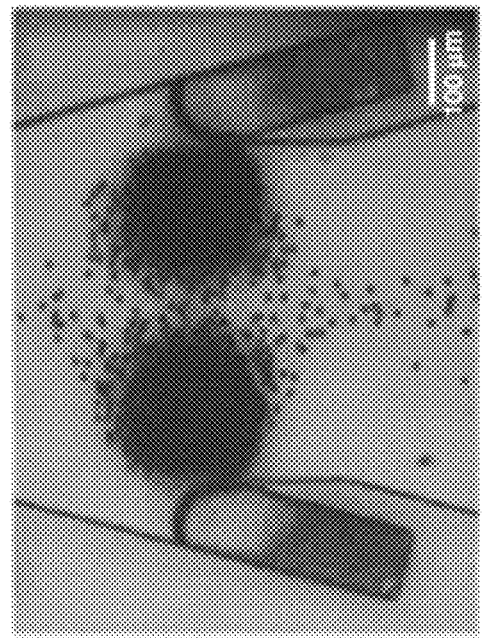

In one method, to increase the purity and ER, a voltage switching procedure is applied by using a short pulse at low voltage while keeping bulk flow at the same rate ($U_b$). FIG. 7C shows that when $U_s$ decreases by reducing the PZT voltage to 2 Vpp, the increase in $U_b/U_s$ ratio allows 10 µm particles to be released. To prevent 15 µm particles from releasing, this voltage is maintained for only 30 seconds. After that, the flow from the syringe pump was switched off and the voltage was increased to 3.5 Vpp for 1.5 min to remove 10 µm particles by the LCATs own ability of generating bulk flow. In this embodiment the device and procedure removed 78.2% of non-target 10 µm particles, and achieved a 30×ER.

Figure 7D:
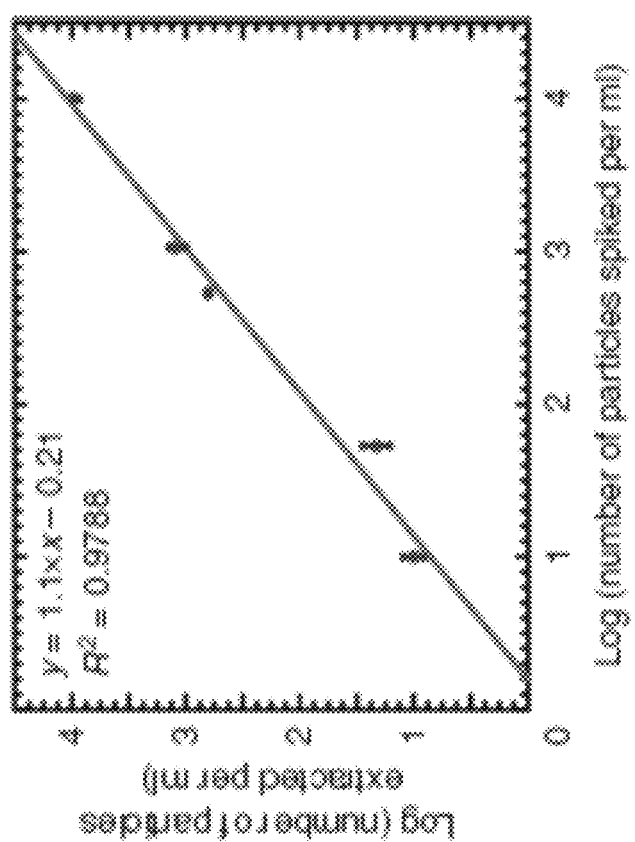
Figure 7E:
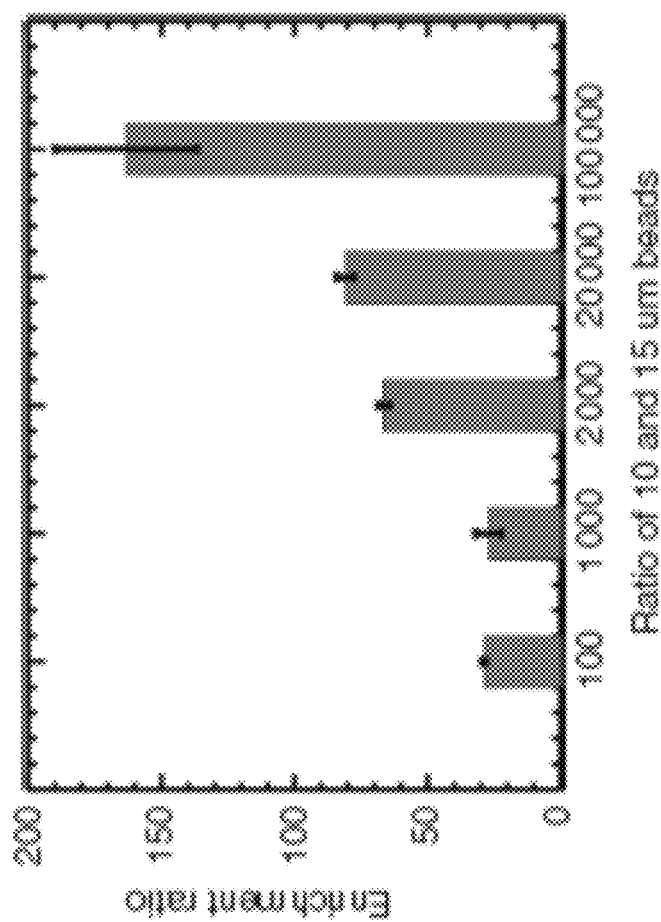

In another embodiment, FIGS. 7D and 7E show the testing at a practical cancer cell occurrence rate, whereby the spiking concentration of 15 µm particles is reduced to 10/ml. The device was able to achieve a 170×ER with approximately 100% trapping efficiency.

Figure 8A:
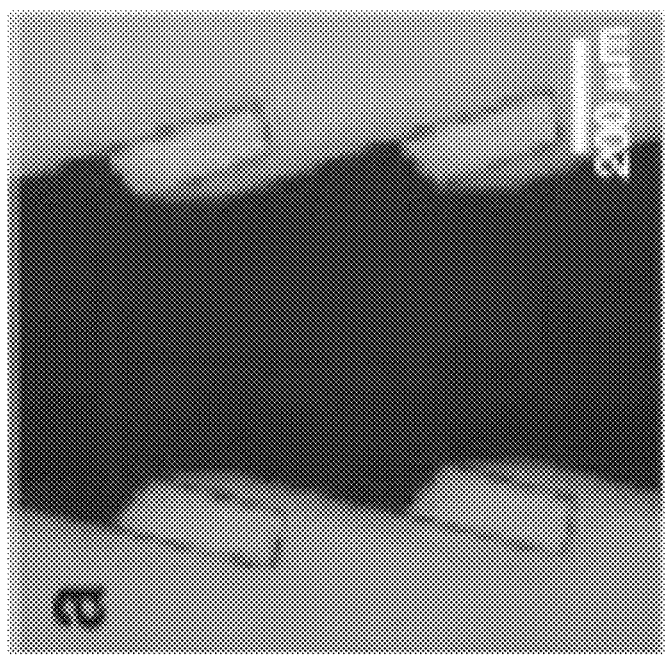
FIGS. 8A-8F show the effective use of a pump to aid in isolating rare particles from a blood sample.
Figure 8B:
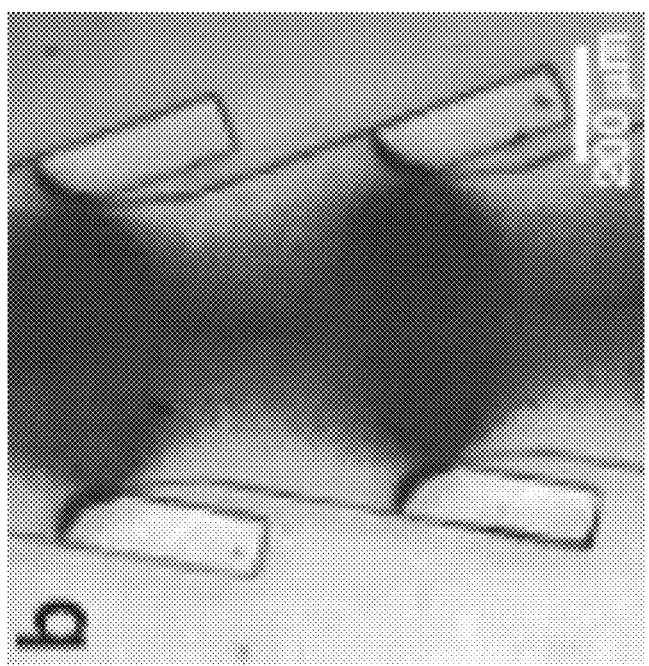
Figure 8C:
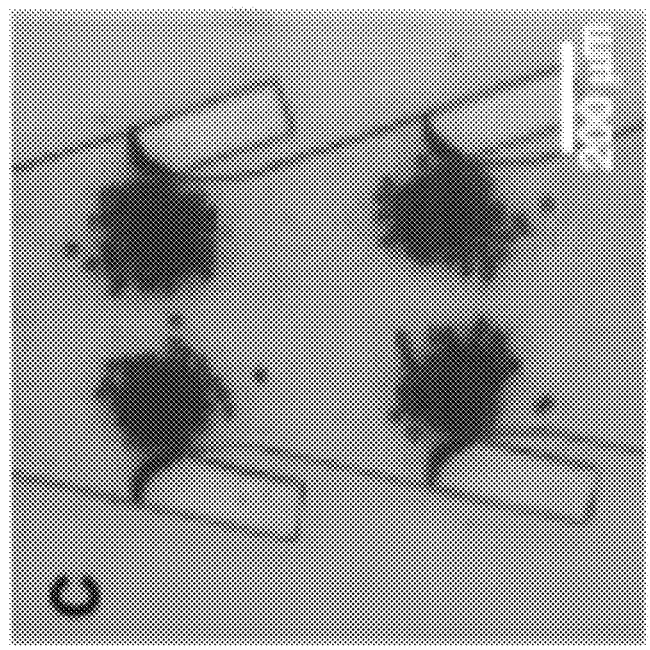

In one example the ability to isolate particles from normal whole blood was tested. FIGS. 8A-8F depict an experiment where 25 µm and 15 µm particles were combined at concentrations ranging from 10,000 ml$^{-1}$ to 10 ml$^{-1}$. In this experiment, flow for the spiked sample was 25 µl min$^{-1}$ and the particles were trapped at 2.75 Vpp. FIG. 8A shows an image of the device using an upright microscope equipped with a high-speed phantom camera, showing the channel filled with RBCs. FIGS. 8B and 8C show the effects of 14 minutes of flow, followed by switching the valve to introduce the wash buffer (1×PBS) at the same flow rate for 20 minutes, with voltage switching to maximize the release of non-target particles. In comparison to FIG. 8A, the washing step begins to remove unwanted particles from the apparatus. As seen in FIG. 8C, this achieves highly pure vortices with 25 µm particles trapped within the vortices.

Figure 8D:
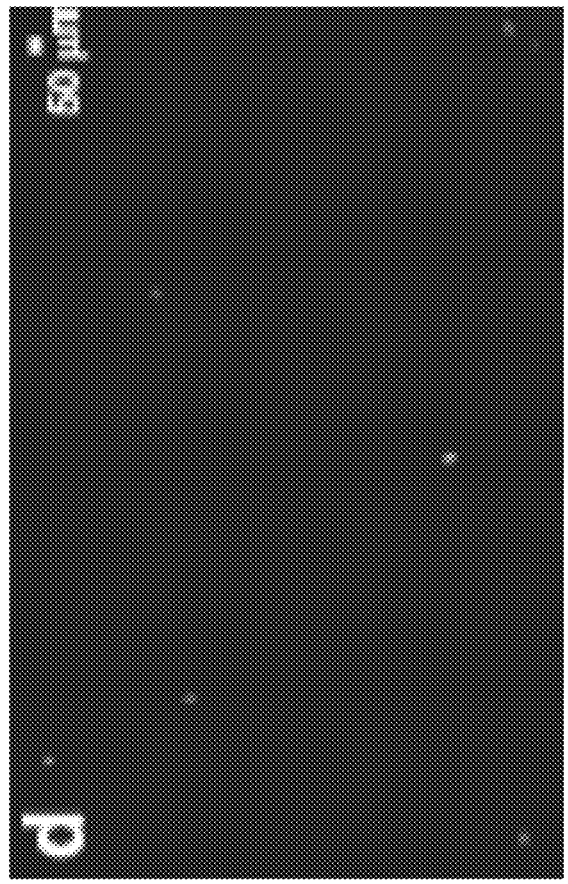
Figure 8E:
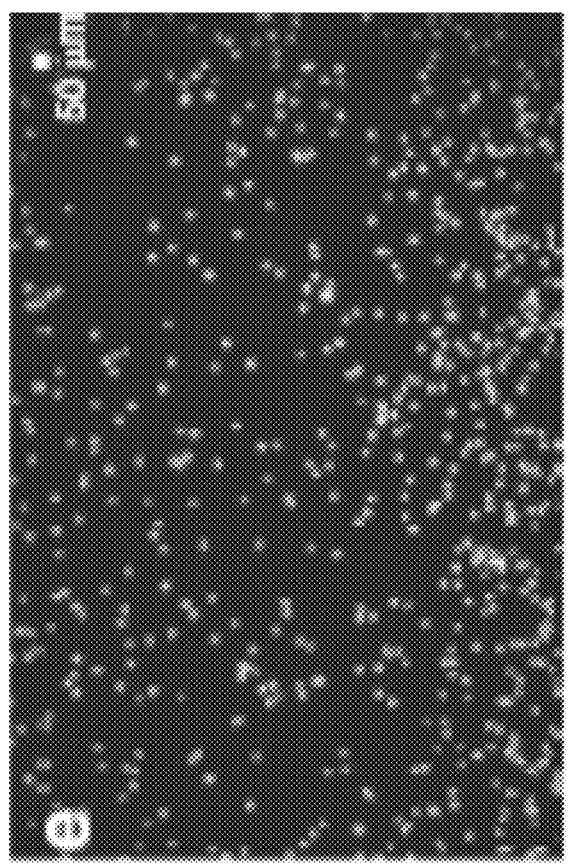

In one embodiment, the device is able to enrich target cells in small volumes. This is a major advantage for the downstream processing of target cells, such as genomic analysis. In one example, after operating the device for 34 min, the PZT was switched off and the trapped cells were released in a 20 µl volume of buffer. The original and trapped sample on a countess slide using fluorescent imaging as shown in FIGS. 8D and 8E demonstrate the ability of the device for significant enrichment. FIG. 8D shows the fluorescent image of the initial spiked blood with 25 µm particles at 10,000/ml concentration. FIG. 8E shows the fluorescent image of enriched 25 µm particles after release from the device. At the higher concentration of particles, 10,000 ml$^{-1}$ with WBCs at the original concentration of 1,000,000 cells per ml, the ER of the particles with respect to WBCs was 70×.

Figure 8F:
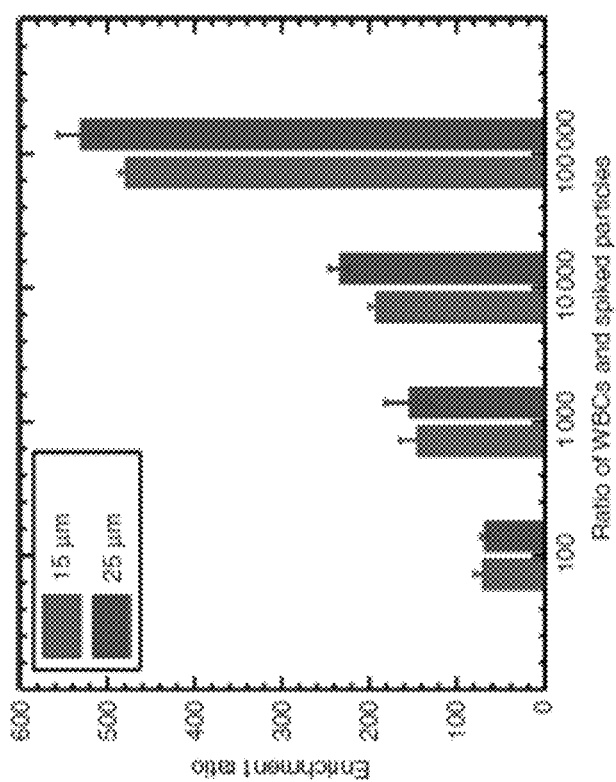

In one embodiment, the same procedure was repeated at lower particle concentrations and achieved a 479×ER for 15 µm particles and 531× for 25 µm particles at 10 ml$^{-1}$ (15 µm and 25 µm at an initial ratio of 1:100,000) spiking concentration as shown in FIG. 8F.

Cell Separation by the Apparatus

It is desirable to show that the methods and the device are effective in separation of cells. In general, the size of circulating tumor cells ranges from 15-25 µm. Whole blood cells are on average approximately 10 µM in size. The separation and enrichment of MCF-7 breast cancer cells from whole blood was demonstrated. MCF-7 cancer cells in suspension were immunofluorescently stained with anti-EpCAM antibody and then spiked into normal donor whole blood at concentrations ranging from 1,000 ml$^{-1}$ to 10 ml$^{-1}$.

Figure 9:
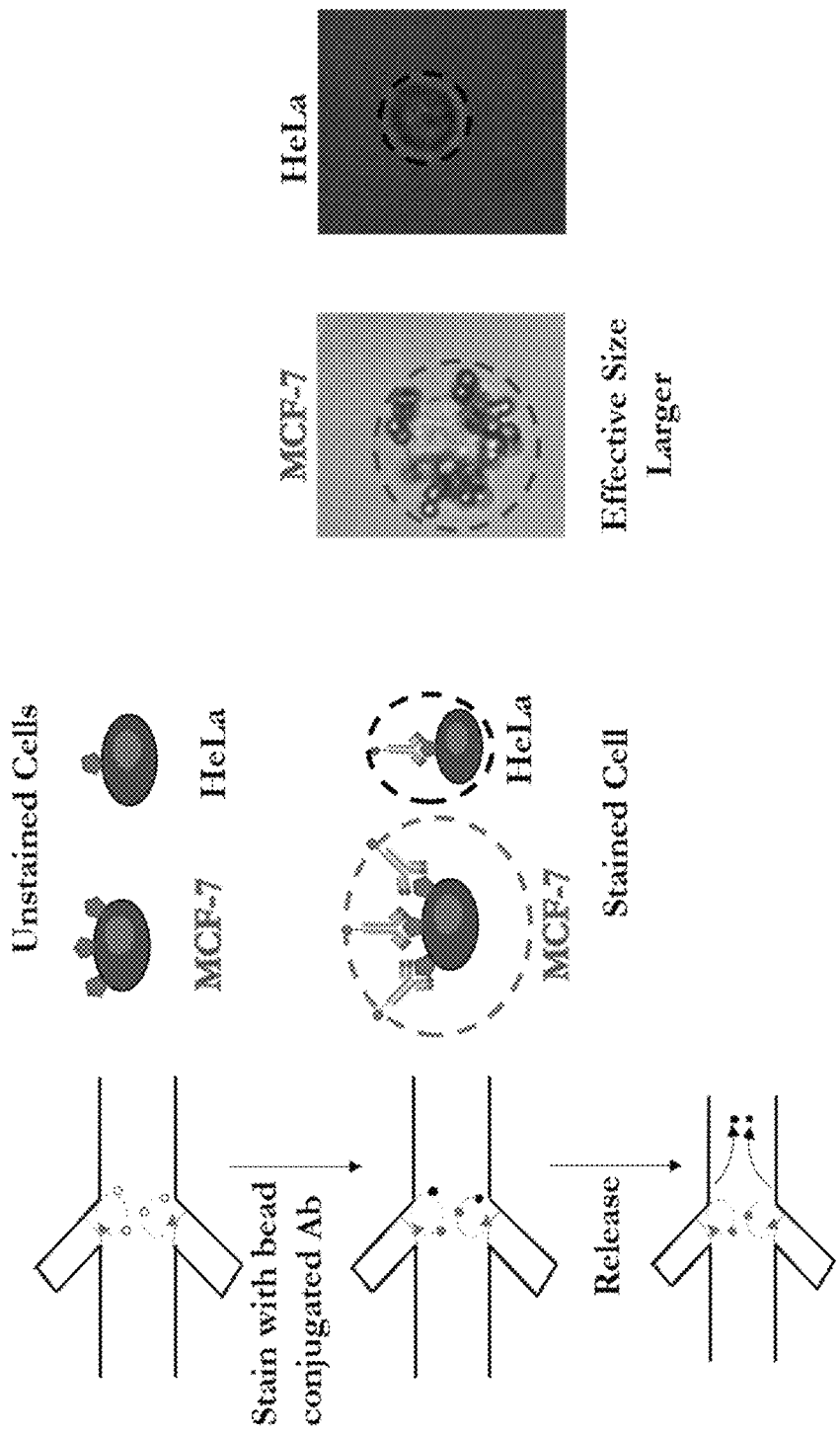
FIG. 9 shows how antibodies can selectively bind to cells thereby increasing cell size and aid in sorting a cell population with the device.

In one embodiment of the invention, antibodies or other selective markers may combine with cells to increase the overall cell size and aid in cell separation. As shown in FIG. 9, the effect of using the antibody is to selectively increase the size of target cell populations. Essentially, this allows selective separation based on size since the antibody will combine with only one component, in this case the cancer cell, but will not combine with the non-cancerous cells. The advantage of using such a method is that even in a mixed population, similar sized cells can be selectively labeled, causing an increase in size and then be sorted accordingly.

Figure 10A:
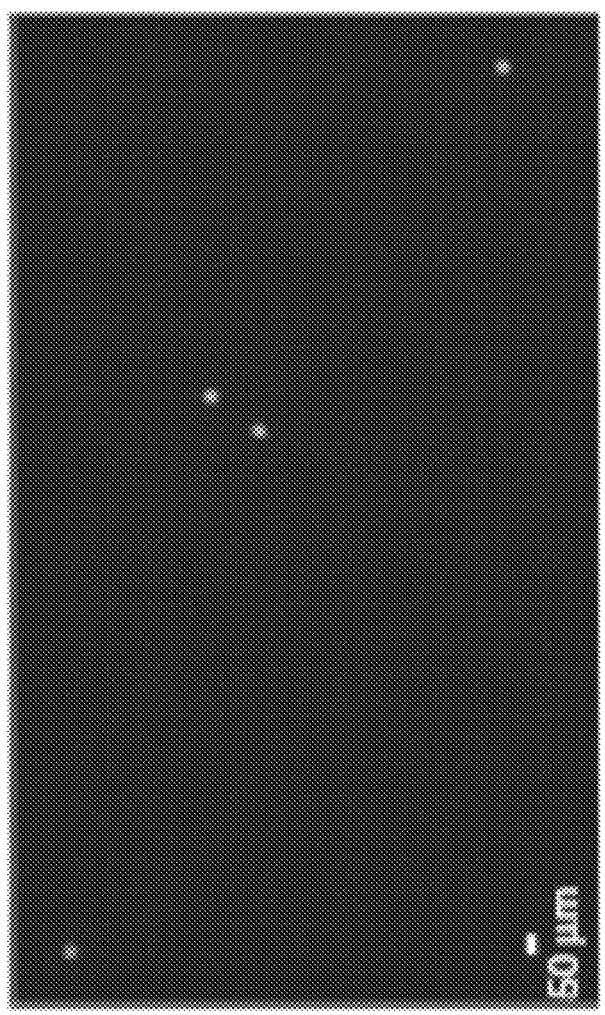
FIGS. 10A-10F show the device is capable of isolating rare cells from a sample are still viable.
Figure 10B:
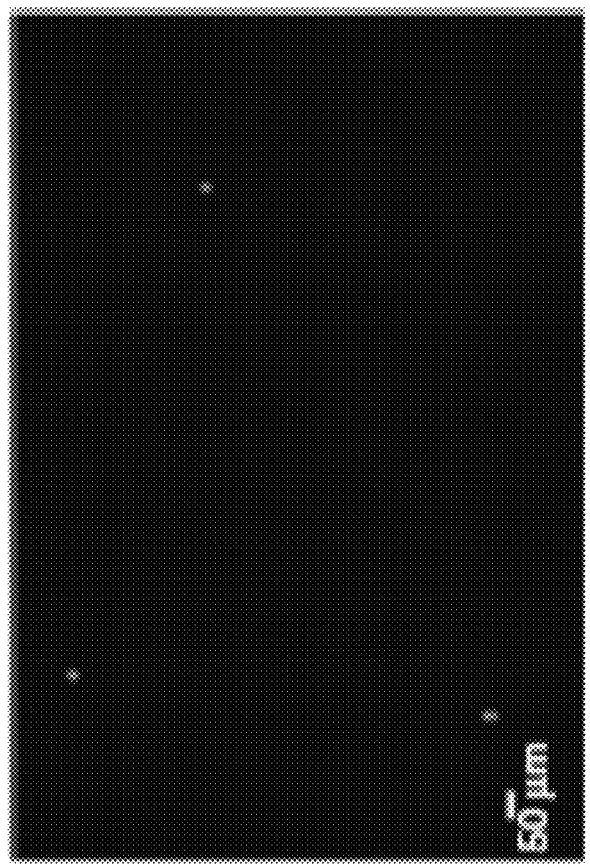
Figure 10C:
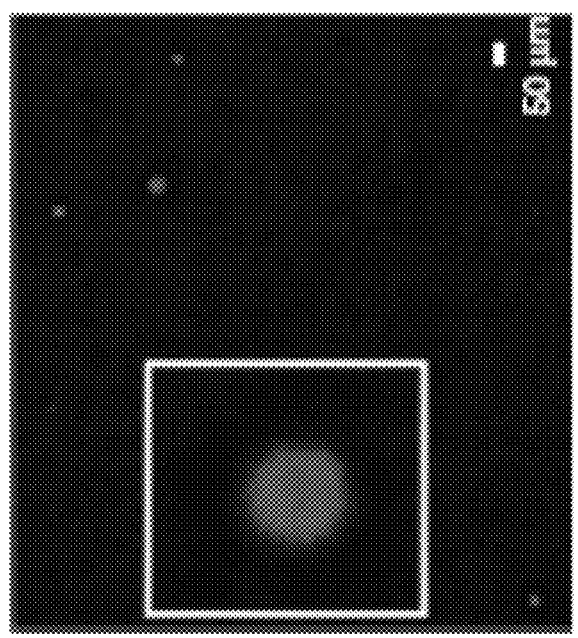
Figure 10D:
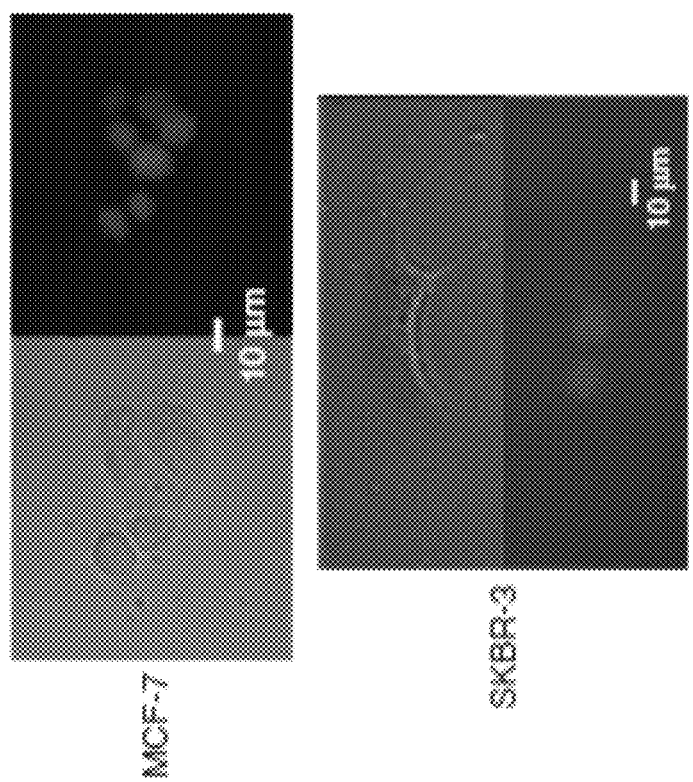
Figure 10E:
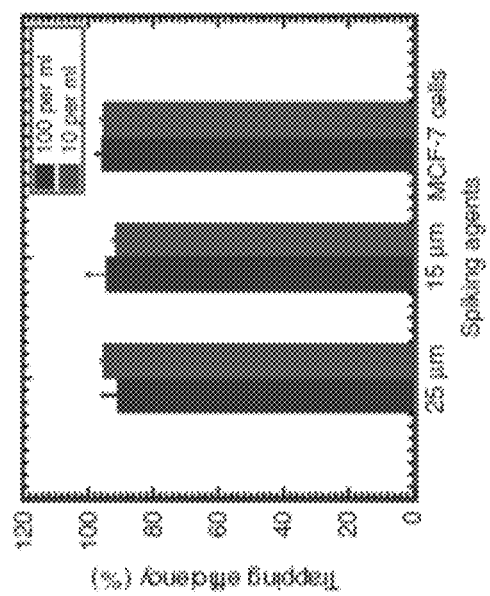
Figure 10F:
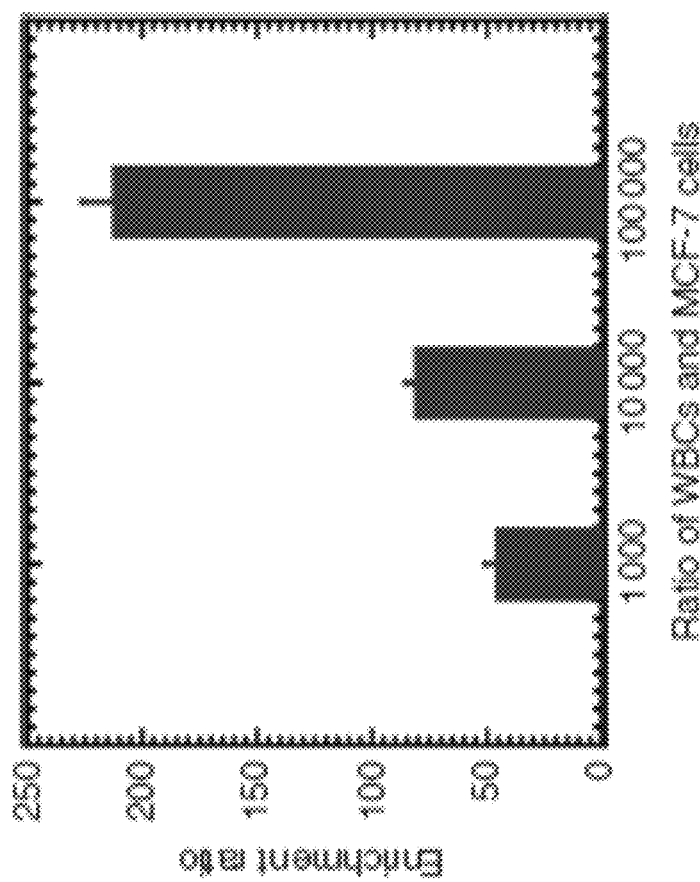

In one experiment, after processing 400 µL of spiked blood sample (separately spiked with 25 µm particles, 15 µm particles, and MCF-7 cells) for 34 minutes, 3-4 particles and 4 cells were captured. FIGS. 10A and 10B show the imaging of the 25 µm and 15 µm captured particles. FIG. 10C shows the fluorescent imaging of 4 MCF-7 cells sorted by the device. These cells were captured when they were spiked at initial concentrations of 10 ml$^{-1}$ in whole blood. This demonstrates an approximate 100% trapping efficiency (FIG. 10E). The MCF-7 cells in the final sample yielded a 213×ER at a 10 ml$^{-1}$ spiking concentration (FIG. 10f).

Cells Survive Separation when Using the Apparatus

In one embodiment, the cells that are captured are intact and able to be cultured. MCF-7 and SKBR-3 cells were cultured for 3 days in media to ensure the preservation of phenotypic and genotypic characteristics after the collection. The cells were imaged as shown in FIG. 10D. FIG. 10D shows the immunostained MCF-7 and SKBR-3 cells in culture with DAPI antibody highlighting nuclear DNA. The intact membranes in bright field (MCF-7 left and SKBR-3 top) and the concentrated nuclear DNA observed by fluorescent imaining (MCF-7 right and SKBR-3 bottom) show the cells are intact and viable.

Forming the Microfluidic Devices

Forming the microfluidic device can first involve drawing micron-scale features using AutoCAD or other drafting tool. The features can then be printed on a transparency mask. These features can then be etched on the silicon wafer using UV lithography or other micron-scale manufacturing technique. After the silanization of the silicon mold, the devices can be made by soft lithographic techniques, such as using PDMS. Priming is done in the devices using a syringe pump at an appropriate flow rate, such as a flow rate of 10 µL/min.

Advantages

The method for interface stabilization increases the lifetime of a lateral cavity acoustic transducer (LCAT) device or similar microfluidic device by preventing the air trapped in the LCAT side channel from being depleted prior to completing the sorting of sample. The device is compatible with pumps to help process large samples and allows elution of cell populations at low volumes. This increases the ability of the device to be used for the enrichment of rare cell/particles in the sample. Further, the sorted and labeled cells preserve both cellular phenotype and genotype as evidenced by continued cell viability.

In situ labelling reduces the complexity and time of conventional processes, such as centrifugation and incubation. By both sorting and labeling the sold sample constituents of interest in the microfluidic device the cost and analysis time can be greatly reduced bringing diagnostic and research capabilities to more and more users.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Some embodiments have been described in connection with the accompanying drawings. However, it should be understood that the figures are not drawn to scale unless otherwise indicated. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method for visualizing cells in a biological sample, comprising:
   obtaining a microfluidic device comprising a lateral cavity acoustic transducer (LCAT) microfluidic channel that extends from an inlet past an array of cavities disposed along the length of the microfluidic channel, each of the cavities being enclosed on one end and exposed to the microfluidic channel through a junction opposite the enclosed end such that each of the cavities can be occupied by a gas;
   priming the LCAT microfluidic device with an aqueous solution, wherein the aqueous solution fills the microfluidic channel but not the array of cavities;
   combining with the biological sample a selective marker that binds to and increases the size of constituents of interest in the biological sample;
   introducing a volume of the biological sample into the aqueous solution in the microfluidic device;
   oscillating a gas-liquid interface at the junction of each of the cavities to trap the constituents of interest in the biological sample in the microfluidic channel adjacent to the junction in a vortex comprising a microstreaming flow pattern, wherein the constituents of interest are trapped because of their increased size from being bound to the selective marker; and
   imaging the selective marker bonded with the constituents of interest to identify the presence or concentration of the constituents of interest in the biological sample.

2. The method of claim 1, wherein the constituents of interest comprise cancer cells.

3. The method of claim 1, wherein the constituents of interest comprise cancer-associated constituents.

4. The method of claim 1, wherein the biological sample is a blood sample that comprises at least one of: whole blood or a volume of blood suspended in a liquid medium.

5. The method of claim 1, wherein the constituents of interest are at a concentration of as low as 10 constituents of interest/mL in the biological sample.

6. The method of claim 1, wherein the microfluidic device comprises an array of cavities arranged along opposite sides of the microfluidic channel.

7. The method of claim 1, further comprising enhancing the concentration of the constituents of interest at the location of the microfluidic channel.

8. The method of claim 1, further comprising increasing the magnitude of the oscillation of the gas-liquid interface to allow constituents of the sample that are smaller than the constituents of interest to flow past the location of the microfluidic channel exposed to the cavity.

9. A method of identifying constituents of a sample, comprising:
flowing a first liquid into a lateral cavity acoustic transducer (LCAT) microfluidic device comprising a lateral cavity acoustic transducer microfluidic channel that extends from an inlet past an array of cavities disposed along the length of the microfluidic channel, each of the cavities being enclosed on one end and exposed to the microfluidic channel through a junction opposite the enclosed end such that each of the cavities can be occupied by a gas;
priming the LCAT microfluidic device with an aqueous solution, wherein the aqueous solution fills the microfluidic channel but not the array of cavities;
trapping constituents of interest in a main channel of the LCAT microfluidic device adjacent to lateral channels thereof by oscillating the LCAT microfluidic device;
flowing a selective marker that binds to constituents of interest into the LCAT microfluidic device while the constituents are trapped, such that the marker combines with the constituents of interest if they are present; and
determining of the constituents of interest are present, wherein if they are present, the method comprises identifying a number or a concentration of the constituents of interest by identifying the number or concentration of markers present in an output of the sample following the flowing of the marker into the LCAT microfluidic device.

10. The method of claim 9, wherein the first liquid comprises at least one of: an aqueous medium or a lipid medium.

11. The method of claim 9, wherein the constituents of interest are at a concentration of as low as 10 constituents of interest/mL in the biological sample.

12. The method of claim 9, wherein the microfluidic device comprises an array of cavities arranged along opposite sides of the microfluidic channel.

13. The method of claim 9, further comprising enhancing the concentration of the constituents of interest at the location of the microfluidic channel.

14. The method of claim 9, further comprising increasing the magnitude of the oscillation of the gas-liquid interface to allow constituents of the sample that are smaller than the constituents of interest to flow past the location of the microfluidic channel exposed to the cavity.

* * * * *